United States Patent [19]

Dietrich et al.

[11] 3,941,126
[45] Mar. 2, 1976

[54] APPARATUS FOR LONG TERM INTRAVENOUS ADMINISTRATION OF DILUTED INCOMPATIBLE MULTIPLE MEDICATIONS

[76] Inventors: Joseph W. Dietrich, 4653 Bromfield Ave., Virginia Beach, Va. 23455; Eugene J. Lubimov, 668 Sirine Ave., Virginia Beach, Va. 23458

[22] Filed: Aug. 8, 1974

[21] Appl. No.: 495,652

[52] U.S. Cl. ...... 128/214 R; 128/214 C; 128/214.2; 222/81
[51] Int. Cl.² ........................................... A61M 5/14
[58] Field of Search ........ 128/214 R, 214 A, 214 C, 128/214.2, 227; 222/80, 81, 426, 430

[56] References Cited
UNITED STATES PATENTS

| | | | |
|---|---|---|---|
| 1,236,865 | 8/1917 | Pittenger | 128/213 |
| 2,254,994 | 9/1941 | Butland | 128/214 A |
| 2,884,924 | 5/1959 | Shaw | 128/214 C |
| 2,954,028 | 9/1960 | Smith | 128/214 R |
| 3,595,231 | 7/1971 | Pistor | 128/215 |
| 3,776,229 | 12/1973 | McPhee | 128/214 C |
| 3,822,700 | 7/1974 | Pennington | 128/214 C |

Primary Examiner—Dalton L. Truluck
Attorney, Agent, or Firm—B. B. Olive

[57] ABSTRACT

An apparatus for intravenous administration of multiple medications of types which tend to be incompatible provides means for diluting the medications separately with a diluent drawn from a common diluent source and for combining the diluted medication at a site proximate to the point of venous entry in order to reduce the opportunity for the medications to mix externally of the body.

10 Claims, 11 Drawing Figures

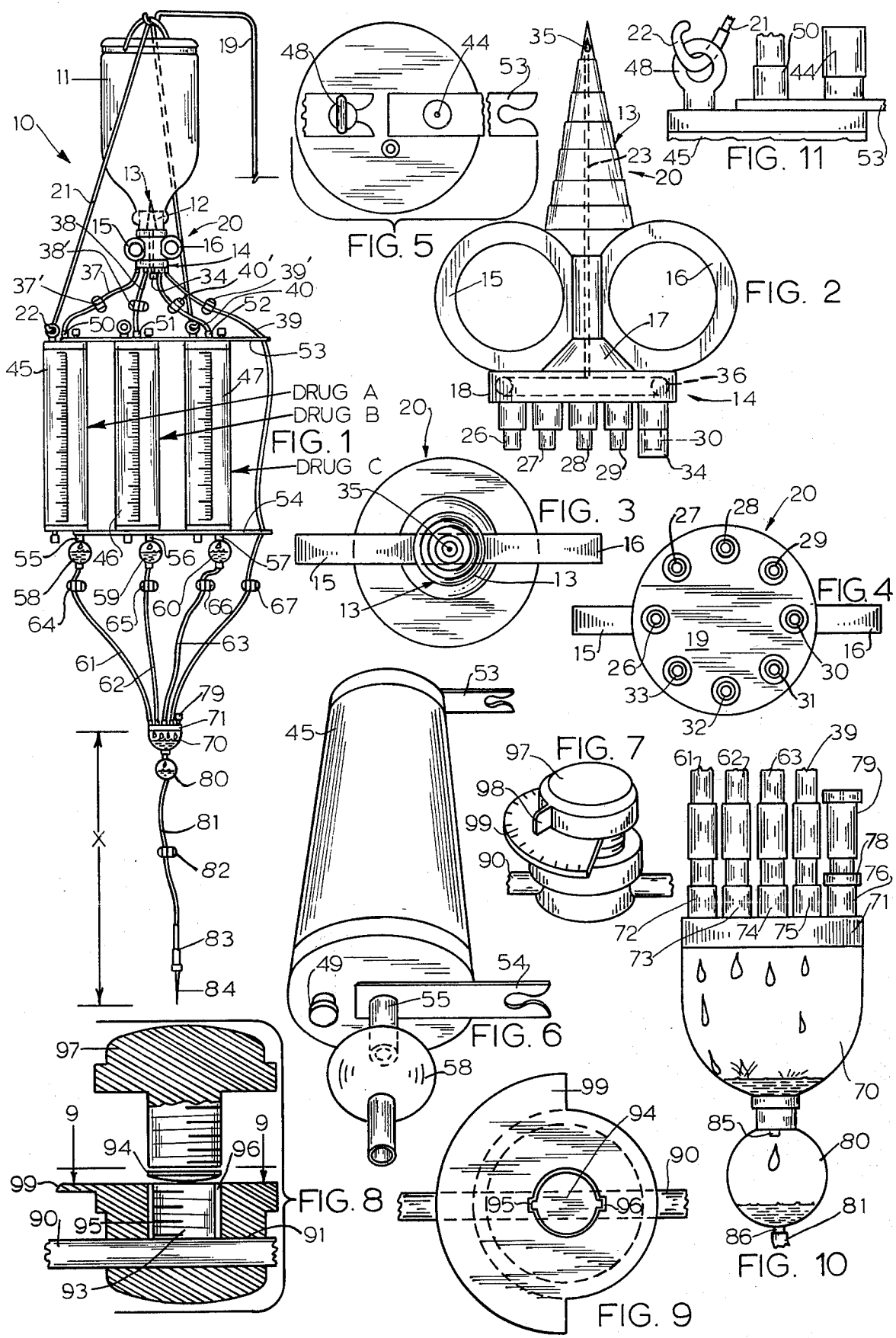

APPARATUS FOR LONG TERM INTRAVENOUS ADMINISTRATION OF DILUTED INCOMPATIBLE MULTIPLE MEDICATIONS

BACKGROUND OF THE INVENTION

1. Field of the Invention

The apparatus of this invention is related to intravenous administration of medications and fluids and particularly to multiple administration of medications and fluids which have physio-chemical incompatibilities.

2. Description of the Prior Art

While vast forward steps have been made in recent years in the development of medications and fluids to be administered to patients, the mechanical art of administration has not kept pace with these scientific developments. The apparatus for administering such medications and fluids intraveneously in the patient, have led to a more or less standard type of infusion set which is comprised of a solution bottle having a stopper apertured for puncturing and venting, a spike or cap device which allows a tube to be connected to the bottle contents through puncturing the bottle stopper, the tube which connects the bottle to the needle, a drip chamber or indicator, and a means of flow control comprising a pinch clip or cock. When a plurality of fluids and medications are to be administered simultaneously, it has been necessary to use a separate needle, tubing and venipuncture for each solution, or to use one or more Y-tubes. Two, three and even four way stop cocks have been employed, and very frequently the flow from two or more fluids or medications, even though incompatible, have been combined and been given the opportunity to mix over a long time prior to entry into the body. Another system of administration is designed to permit the contents of two or more intravenous solution bottles to flow into a patient while all are connected together. Such a system allows an unlimited number of bottles to be connected in "series."

Today, fluids such as saline, dextrose and lactated fingers, to name a few, are administered by infusion using special equipment. The equipment is sterile, disposable and subject to stringent controls in the hospitals. An increasing hospital practice for the administration of medications is to combine them with such fluids. Many of these are life saving drugs and by their nature are administered intravenously quite often; in some cases, there is no other choice. Today, it is a very common practice for a physician to order three or more drugs to be administered simultaneously to the patient. Many of these drugs have chemical and physical incompatibilities and which is of special significance to the invention.

Numerous references are available concerning the critical problem of medication incompatibilities. The Norfolk General Hospital, Pharmacy Service, publication entitled "Intravenous Fluids, Incompatibility Guide" cites many such references and lists the following factors which may cause incompatibilities:

| | |
|---|---|
| Preservative of Drug | Oxidation |
| Preservative in Diluent | Reduction |
| Buffering Agents | Photosensitization |
| Antioxidants | Inactivation |
| Vehicle | Order of Mixing |
| Changes in pH | Period of Standing |
| Molecular Complexation | Brand of Drug |
| Supersaturation | Neutralization |
| Change in Viscosity | Precipitation |
| Particle size distribution | Improper Dilution |

There are a number of ways to handle the incompatibility problem, all of which are presently unsatisfactory. The common method is to add one drug to the basic fluid in a burrett device and infuse it over an hour, then add the second drug, etc., thus consuming an inordinate amount of nursing time. Physicians and nurses are often concerned with such matters as the Ph of a fluid or its chemical and physical incompatibilities. The majority of incompatibilities are kinetically slow in developing, which necessitates the use of small volumes of basic infusion fluid as a diluent in a burrette device in contrast to placing all of the drugs to be administered in the 8 hour period in one large volume container. In many United States hospitals, the pharmacy has developed an intravenous (I.V.) fluid admixture service. The I.V. drugs are reconstituted and/or packaged aseptically in suitable small volume containers to be added by the nurse to existing I.V. infusions. Another practice is to actually prepare the large volume I.V. infusion which contains the drugs in labeled containers which are delivered to the nurse for subsequent administration. With the hospital pharmacist becoming more involved in intravenous admixture preparation and monitoring, the need for more accurate and dependable systems of delivery for incompatible medications is of paramount importance.

SUMMARY OF THE INVENTION

This invention is an improvement on the equipment now in use for diluting, storing prior to administration, and administering of multiple medications and fluids where the same are for some reason incompatible in the sense previously discussed. A spike or piercing pin has integral finger grips and is adapted to be universal for insertion into the stopper, which is normally of rubber, of any of a number of diluent fluid bottle types. A manifold structure is made integral with the universal spike and functional engagement of the spike with the resilient stopper provides support for the integral spike-manifold structure. The manifold receives the fluid from the inserted spike and directs it out through a plurality of discharge ports and into a number of flexible intake tubes. Each intake tube transfers the fluid into a calibrated medication chamber or one or more tubes can bypass these chambers if so desired. The calibrated chambers act as infusion containers and are arranged so that they can be releasably secured together in a side-by-side relation. Once within the calibrated medication chamber, the fluid and a medication, previously placed in the respective chamber, mix and form a solution. Thus, each chamber acts as a means for diluting with a common fluid a particular medication and for keeping such diluted medication isolated from diluted medications in other chambers. A discharge tube discharges the fluid-medication solution from the base of each calibrated chamber. Each discharge tube, except for the bypass tubes, includes in its path an individual drip chamber and an individual regulator valve which allows for display and individual control of the rate of discharge of each respective solution. Thus, each fluid medication solution can be individually regulated.

A common drip chamber is located immediately adjacent the injection site and has a manifold head which connects to the discharge tubes including any bypass discharge tube. This last mentioned drip chamber thus allows for final mixing of all fluid-medication solutions and all bypassed fluid immediately prior to administration into the patient's vein. A final regulator valve is situated in the tube leading to the injection site and provides for control of the rate of discharge of the final solution. This last mentioned tube is connected to a conventional needle adaptor which in turn mounts a suitable needle for insertion into the vein of the patient.

In summary, the apparatus of the invention provides a multiple drug and fluid infusion system wherein incompatibilities are kept to a minimum since contact time of drugs is kept at a minimum, when in a mixed state external of the body. Several other improvements and advantages over presently existing devices are: (a) additional drugs can be added to the infusion set without disruption of previous infusion parameters, (b) rates of infusion can be controlled independently of each other, (c) when drugs are discontinued by the physician, the remaining drugs can be administered without waste, and (d) drugs in separate chambers or burrettes will not mix.

DESCRIPTION OF THE DRAWINGS

FIG. 1 is an elevation view of an assembly of apparatus incorporating the present invention.

FIG. 2 is an enlarged elevation view of the integral universal spike-manifold employed by the invention.

FIG. 3 is a plan view of the integral universal spike-manifold employed by the invention.

FIG. 4 is a bottom view of the integral universal spike-manifold.

FIG. 5 is a plan view on a reduced scale of one of the calibrated solution chambers.

FIG. 6 is a perspective view of a calibrated solution chamber and showing a drip chamber located adjacent the base thereof.

FIG. 7 is a perspective view of a regulator valve employed with the invention for controlling rate of flow.

FIG. 8 is a partial section, enlarged exploded elevation view of the regulator valve.

FIG. 9 is a plan view taken along line 9—9 of FIG. 8.

FIG. 10 is an enlarged elevation view of the solution mixing chamber and associated drip chamber.

FIG. 11 is a partial elevation view of the top portion of one of the calibrated solution chambers.

DESCRIPTION OF THE PREFERRED EMBODIMENT

Referring now to the drawings in detail wherein like numbers pertain to like parts, reference is first made to FIG. 1 wherein the entire apparatus of the preferred embodiment of the invention is shown.

The apparatus of the invention is directed to distributing a common diluent to a plurality of diffusion chambers, allowing otherwise incompatible medications to combine with the fluid mix therein and then directing all of the combined medications to the site of injection. Such apparatus is generally designated as 10. A standard, sterile fluid filled container or bottle 11, of the type capable of being suspended from support 19 while inverted has a rubber or like resilient stopper 12 sealing its top and which is conventionally provided with a preformed puncturing aperture and vent aperture. The spike-manifold structure 20 has a universal spike or piercing pin 13 which is adapted to be inserted into the center of stopper 12 of bottle 11. Spike 13 is preferably of a stepped, tapered design as illustrated which makes it adaptable for use with various sizes of puncturing apertures and thus with practically all standard bottles 11. A housing portion 14 of spike 13 has made integral therewith finger grip members 15, 16. Base 17 of housing 14 flares outwardly and forms a manifold 18. Manifold 18 has several discharge ports 26 through 33 enabling the fluid from bottle 11 to be distributed to a plurality of diffusion containers as later described. An opening 35 in the tip of spike 13 connects to a central bore 23 which extends through spike 13 and communicates with a cavity 36 in manifold 18. Ports 26 through 33 have, when not in use, covering caps 34 (FIG. 2) which close off manifold 18 to prevent flow of fluid therefrom and to prevent entry of germs, and the like.

Flexible conduits or tubes 37, 38, 39, 40, only four being shown for purpose of illustration, are preferably adapted at one end with suitable couplers for quick coupling to any of discharge ports 26 through 35 and at the other end for quick coupling to any of calibrated containers 45, 46, 47 through their respective intake ports 50, 51, 52. Also, a conduit can be arranged to by-pass the calibrated medication chambers 45, 46, 47 as does conduit 39. Such an arrangement allows a controlled quantity of diluent to be added to the composite mix of diluted medications in chamber 70 immediately prior to injection. Tubes 37, 38, 39, 40 are preferably provided with conventional pinch valves 37', 38', 39' and 40'. The fluid filled containers may average about 160 grams each in weight. Support for containers 45, 46, and 47 is provided. In the embodiment illustrated, a flexible wire 21 has a hook 22 which engages one of the eyelet knobs 48 and wire 21 is otherwise passed through other respective eyelets provided by eyelet knobs 48, as best shown in FIGS. 1 and 11, and appropriately tied.

Containers 45, 46, 47 are intended to serve as containers for holding three separate medications, e.g., medications A, B and C and for allowing these to be separately diluted with the appropriate diluent from bottle 11. To facilitate the coordination of the separate mixing operations, each container is provided with top and bottom holders 53, 54 having resilient slotted ends as shown which snap-fit to corresponding eyelet knobs 48 (FIG. 5) and knobs 49 (FIG. 6). Holders 53, 54, as illustrated, comprise thin bars which are glued, welded or otherwise secured to the respective containers 45, 46, 47. Eyelet knobs 48 serve both to receive wire 21 for support purposes and as a means for securement to the holders 53, 54. Containers 45, 46, 47 are further provided with appropriate air vents 44 and with respective discharge ports 55, 56, 57, from which the respective mixed medication diluent solutions are allowed to exit. Each discharge port 55, 56, 57 connects to respective drip chambers 58, 59, 60, which in turn connect to respective tubes 61, 62, 63 having respective regulator valves 64, 65, 66 which provide for individual control of rate of discharge of each medication-diluent solution. While not shown, bypass line 39 may also include a drip chamber. Bypass line 39 also has an individual regulator valve 67 which controls the rate of direct flow of fluid from bottle 11 into a common drip, mixing chamber 70, which is located immediately adjacent, or as close as practical, to the injection site.

A manifold head portion 71 in chamber 70 receives the various medication-diluent solutions through inlet ports 72-75 and directs them to chamber 70 proper to be mixed with whatever amount of diluent is allowed to flow through tube 39. Conduits 61, 62, 63 and 39 preferably utilize quick connect couplings and any unused inlet port, e.g., inlet port 76, can be closed off by using a suitable top 78 which keeps mixing chamber 70 free of contamination. An air filter 79 (FIG. 1) is placed on one of the manifold head inlet ports as required. It should be noted that chamber 70 allows for the first mixing of all the medication-drug solutions and immediately prior to administration into the patient's vein. A common drip chamber 80 is located immediately adjacent and below mixing chamber 70 and a short conduit 81 extends from chamber 80 to provide a final path for the mixed solutions to the needle insertion point. For purposes of being able to control the flow of the mixed solutions, it is noted that the exhaust port 85 for chamber 70 should be sufficiently larger than the exhaust port 86 of the drip chamber 80 to allow a visible accumulation of liquid in drip chamber 80.

Flow through conduit 81 to the needle site is controlled by a final regulator valve 82. Conduit 81 connects to a needle adapted 83 which in turn mounts a suitable needle 84 for insertion into the vein of the patient. With the described invention system, distance X (FIG. 1) should and can be kept minimal in order to minimize the described incompatibility effect.

Referring to FIG. 1, an application of the present invention apparatus 10 will be described. It is assumed that a doctor needs to administer given quantities of three drugs A, B and C which are placed in respective containers 45, 46 and 47 and are to be mixed with a basic fluid or diluent D. However, it is assumed that drug A is not compatible with drug B and drug C is not compatible with either or the combination of drugs A and B. By compatibility is meant chemical and physical compatibility external of the body as related to any of the recognized compatibility factors previously mentioned or other factors of the same effect. Once in the vein, drugs will normally distribute in the body in approximately 15 seconds provided adequate circulation exists; therefore, the primary problem dealt with by the invention concerns compatibility external of the body.

In the assumed example, a suitable diluent filled bottle 11 is suspended and supported, as illustrated. The drug holding calibrated chambers 45, 46, 47 are snap-fitted together by the respective connectors 53, 54 engaging the respective top eyelet knobs 48 and bottom knobs 49 and are suspended below bottle 11 in a laterally aligned and spaced position. Conduits 37, 38, 40 are respectively secured on one side to chambers 45, 46, 47 and on the other side to discharge ports 28, 29, 30 of manifold 18. Spike portion 13 is inserted into rubber stopper 12 of bottle 11 and bypass line 39 is connected to manifold 18 at port 32. Drip chambers 58, 59, 60; conduits 61, 62, 63 and 39 are connected to the respective inlet ports of manifold head portion 71 of common drip, mixing chamber 70. Now drip chamber 80, conduit 81, valve 82, needle adaptor 83 and needle 84 are assembled.

As fluid from bottle 11 drips into chambers 45, 46, 47, a solution of drug and fluid is made in each chamber. As each medication-diluent solution leaves its respective chamber and passes into its respective drip chamber, the solution flows therefrom and its rate of flow is independently adjusted by the respective valves 64, 65, 66 with flow through bypass line 39 being controlled by valve 67. Chamber 70 provides the first inter-drug-diluent solution mixing point for each of the individual solutions prior to administration to the patient. Once needle 84 is inserted into the patient's vein, the system can be started by adjusting to the desired administration rate by setting the appropriate regulator valves. The mixed solution thus travels only over distance "X." In a typical bedside infusion system according to the invention, the distance "X" can be made as short as 72 inches and the approximate time of flow of the mixed drug-diluent solution from chamber 70 to needle 84 can be as low as about 10 ml./hour Thus, opportunity for external incompatible mixing is minimized.

While a wide variety of pinch valves are available, the type pinch valve illustrated in FIGS. 7-9 has been found particularly useful to the invention for purposes of valves 64-67 and 82. In this regard, it will be noticed that the illustrated tube 90 is received by one passage 91 which is perpendicular to the threaded passage 92 and in which the dished plate 94 is loosely guided in slots 95, 96. As threaded knob 97 is turned, plate 94 pinches tube 90 an amount which can be controlled by reference to index point 98 and index plate 99.

The apparatus of the invention thus provides a multiple drug and fluid infusion system wherein incompatibilities are kept to a minimum since contact time of drugs is kept at a minimum. Rates of infusion of the different drugs can be controlled independently of each other. Also, additional drugs can be added to the infusion set without disrupting the previous infusion parameters. If a physician should want to discontinue a particular drug, the remaining drugs can be administered without disturbance.

It will also be appreciated by those skilled in the art that the apparatus described is not limited to the disclosed administration but is also useful in connection with administration of blood, serums, and the like, where there is a fluid incompatibility problem of the kind described. While the invention is shown in connection with three individual drugs, it will be understood that it can be utilized with a single drug or with any number of drugs as desired.

Of particular advantage is the integral spike-manifold structure. The pointed spike body is effectively made up of sections of increasing diameter which make the spike universal for various sized puncturing apertures and thus for resilient bottle stoppers. Also, the tapered, stepped conical formation of the spike enables the spike to be frictionally engaged in such types of stoppers and to provide support for the overall spike-manifold structure. The manifold with its plural discharge ports which connect to the aperture and central passage of the spike insure ease of distribution of the diluent to any comparable number of containers.

Also of advantage to the invention is the mixing and sight assembly composed of mixing chamber 70 and drip chamber 80. This assembly allows a plurality of separate diluent-medication solutions to be received through a manifold and to combine, for the flow rate of each solution to be observed as it enters the chamber from the manifold prior to mixing and allows for all the solutions to leave through a single exhaust port and the flow rate of the combined solutions to be separately observed. Use of the mentioned air filter 79 on chamber 70 when suitably sized prevents pressurization and aids in preventing the situation of fluid from one container going into chamber 70 and then tending to flow to another container rather than out of chamber 70.

What is claimed is:

1. An apparatus for diluting, combining, and intravenously injecting a plurality of potentially incompatible substances including medications comprising, in combination:
   a. a bottle having a penetrable vented stopper and containing a supply of a selected diluent to be withdrawn through the stopper with the bottle inverted;
   b. an integral spike-manifold structure adapted for placement below said bottle and providing a spike adapted to penetrate said stopper and provide a fluid passage therethrough and communicating with said passage a manifold providing a plurality of discharge ports enabling said diluent to be withdrawn from said bottle through said spike and made available for discharge through each of said ports, said manifold structure having a finger grip formation formed integral therewith and adapted to receive an operator's fingers for installing said spike;
   c. a plural configuration of tubes, sight chambers, valves and vertically disposed calibrated transparent containers supported below said bottle and spike-manifold structure and providing means whereby various incompatible substances such as medications may be isolated in measured amounts and diluted with the same said diluent while remaining in isolation from each other and at individually controlled rates of flow therethrough, each container having a top inlet port, a tube connection between such inlet port and a respective said manifold discharge port, a bottom outlet port and a bottom tube connected thereto and leading downward therefrom, each bottom tube having in its path a sight chamber and a regulator valve for individually regulating the flow therethrough;
   d. a mixing-sight chamber having on one upper side a plurality of inlets connected respectively to said bottom tubes for individually receiving and then combining the individually mixed medication-diluent fluids discharged by said containers and on an opposite lower side a discharge port; and
   e. a fluid injection assembly including a tube having in its path a further sight chamber and regulator valve and said assembly being connected on one end to said mixing-sight chamber discharge port and on the opposite end to a needle for vein injection.

2. An apparatus as claimed in claim 1 wherein said spike-manifold structure finger grip formations inlcudes a pair of ring members formed integral therewith and adapted to receive an operator's fingers for installing said spike.

3. An apparatus as claimed in claim 1 including an auxiliary tube connected between a said manifold discharge port and a said mixing-sight chamber inlet and having a regulator valve associated therewith thereby enabling predetermined quantities of said diluent to bypass all of said containers and to initially mix with the contents thereof in said mixing-sight chamber.

4. An apparatus as claimed in claim 1 wherein at least selected ones of said regulator valves include means for effectively pinching the respective said tubes and index means by which the amount of such pinching can be visually observed.

5. An apparatus as claimed in claim 4 wherein each said selected ones of said valves comprise a body member mounting an index plate, a first aperture for receiving the respective tube to be regulated, a second threaded aperture communicating with and axially oriented perpendicular to the first aperture, and having a sliding plate member therein, and a threaded screw member received by said second aperture and adapted upon being turned to press said plate member against the respective tube to effect said pinching and having an appended index enabling said turning to be referenced to said index plate.

6. An apparatus as claimed in claim 1 including connector means on said containers enabling them to be detachably secured together side by side and comprising a pair of opposed connector bars respectively secured on one end to the tip and bottom of each said container and having the opposite end provided with an open-ended slot, and knob members located on said container top and bottom and adapted to be detachably received in said slots to effect said securement.

7. An apparatus as claimed in claim 1 wherein said spike is conical-shaped and the body thereof is formed in portions of increasing diameter and said passage includes an aperture at an outer pointed end of said spike and a channel communicating therewith and extending lengthwise and internally of said body between said manifold and said aperture.

8. An apparatus as claimed in claim 1 including detachably connector means having respective mating portions secured to the respective said containers whereby a plurality of such containers may be secured together in a side-by-side relation.

9. An apparatus as claimed in claim 1 wherein said mixing sight chamber includes an air filter sized to relieve any tendency for said mixing sight chamber to serve as a flow path between said containers.

10. An integral spike-manifold structure for distributing fluid from a bottle having a penetrable vented stopper and a fluid to be withdrawn through the stopper with the bottle inverted, comprising in combination:
   a. a conical-shaped spike portion having a body formed with a pointed end, consecutive body sections of increasing diameter, an aperture in said end and an internal central passage extending through said body;
   b. a pair of ring-shaped members appended to said body and enabling finger grasping of said structure; and
   c. a manifold portion providing a plurality of discharge ports and internal passages connecting said ports to said body passage enabling fluid from said bottle to be withdrawn through said aperture and discharged through each of said ports.

* * * * *

UNITED STATES PATENT OFFICE
CERTIFICATE OF CORRECTION

Patent No. 3,941,126    Dated March 2, 1976

Inventor(s) Joseph W. Dietrich et al

It is certified that error appears in the above-identified patent and that said Letters Patent are hereby corrected as shown below:

In Col. 1, line 18, "intraveneously" should be --intravenously--

In Col. 5, line 25, "adapted" should be --adaptor--.

In Col. 6, line 13, a period should be placed after "hour".

In Col. 8, line 24, "tip" should be --top--.

Signed and Sealed this

Twentieth Day of July 1976

[SEAL]

Attest:

RUTH C. MASON
*Attesting Officer*

C. MARSHALL DANN
*Commissioner of Patents and Trademarks*